United States Patent
Stone (10) Patent No.: US 9,198,673 B2
(45) Date of Patent: Dec. 1, 2015

(54) LOCALIZED CARTILAGE DEFECT THERAPY

(75) Inventor: Kevin T. Stone, Winona Lake, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 884 days.

(21) Appl. No.: 13/350,985

(22) Filed: Jan. 16, 2012

(65) Prior Publication Data

US 2012/0116409 A1     May 10, 2012

Related U.S. Application Data (63) Continuation of application No. 11/739,768, filed on Apr. 25, 2007, now Pat. No. 8,137,354.

(51) Int. Cl.
| | | |
|---|---|---|
| A61F 2/46 | (2006.01) | |
| A61B 17/16 | (2006.01) | |
| A61B 17/30 | (2006.01) | |
| A61B 17/56 | (2006.01) | |

(52) U.S. Cl.
CPC ....... *A61B 17/1635* (2013.01); *A61B 2017/306* (2013.01); *A61B 2017/564* (2013.01)

(58) Field of Classification Search
CPC ............ A61F 2/30756; A61F 2/30767; A61F 2/4618; A61F 2310/00964; A61B 5/4514; A61B 10/025; A61B 10/0283
USPC .......... 623/13.12–13.19, 14.12, 23.48–23.76, 623/908, 923; 606/92–95; 604/68–72, 289
See application file for complete search history.

(56) References Cited

U.S. PATENT DOCUMENTS

| | | | | |
|---|---|---|---|---|
| 3,896,810 A | * | 7/1975 | Akiyama | 604/117 |
| 4,872,450 A | * | 10/1989 | Austad | 602/48 |
| 5,224,940 A | * | 7/1993 | Dann et al. | 604/290 |
| 5,496,290 A | * | 3/1996 | Ackerman | 604/268 |
| 5,662,677 A | * | 9/1997 | Wimmer | 606/201 |
| 5,860,947 A | * | 1/1999 | Stamler | 604/19 |
| 5,871,456 A | * | 2/1999 | Armstrong et al. | 601/14 |
| 6,210,381 B1 | * | 4/2001 | Morse | 604/289 |
| 6,293,929 B1 | * | 9/2001 | Smith et al. | 604/289 |
| 6,309,124 B1 | * | 10/2001 | Gueret | 401/124 |
| 6,334,064 B1 | * | 12/2001 | Fiddian-Green | 600/311 |
| 6,716,190 B1 | * | 4/2004 | Glines et al. | 604/70 |
| 7,771,482 B1 | * | 8/2010 | Karmon | 623/17.17 |
| 7,790,945 B1 | * | 9/2010 | Watson, Jr. | 602/43 |
| 8,088,108 B2 | * | 1/2012 | Kraft | 604/173 |
| 8,361,054 B2 | * | 1/2013 | Ducharme et al. | 604/508 |
| 8,672,904 B1 | * | 3/2014 | Schultz | 604/302 |
| 2002/0111591 A1 | * | 8/2002 | McKinnon et al. | 604/289 |
| 2004/0073176 A1 | * | 4/2004 | Utterberg | 604/256 |
| 2005/0261642 A1 | * | 11/2005 | Weston | 604/313 |
| 2006/0280803 A1 | * | 12/2006 | Kumar et al. | 424/549 |
| 2007/0167926 A1 | * | 7/2007 | Blott et al. | 604/304 |
| 2008/0166421 A1 | * | 7/2008 | Buhr et al. | 424/530 |

\* cited by examiner

*Primary Examiner* — Matthew Lawson
(74) *Attorney, Agent, or Firm* — SCHWEGMAN LUNDBERG & WOESSNER, P.A.

(57) ABSTRACT

An isolation device for repairing a cartilage defect including a syringe and a barrier device. The barrier device is connected to the syringe. The barrier device is sized to surround and contain the cartilage defect, and is configured to provide a seal around the cartilage defect for application of a positive pressure and a negative pressure from the device. The device is configured to provide a localized therapy to the cartilage defect.

19 Claims, 7 Drawing Sheets

FIG. 5E
(SECTION A-A)

LOCALIZED CARTILAGE DEFECT THERAPY

CROSS-REFERENCE TO RELATED APPLICATIONS

This application is a continuation of U.S. patent application Ser. No. 11/739,768 filed on Apr. 25, 2007, the entire disclosure of which is incorporated herein by reference.

FIELD

The present disclosure relates to apparatuses and methods for cartilage defect therapy.

BACKGROUND

The statements in this section merely provide background information related to the present disclosure and may not constitute prior art.

Articular cartilage enables bones to move smoothly relative to one another. Damage to the articular cartilage and the underlying bone can be caused by injury, such as tearing, by excessive wear, or by a lifetime of use. Damage to articular cartilage, particularly of the load-bearing regions may cause pain and reduce mobility. Medical intervention such as medications, therapy, or surgery can be required to restore proper function to the damaged area.

Various cartilage defects are often repaired using arthroscopic procedures to deliver a graft material or a therapeutic material or to perform microfracture. In arthroscopic procedures where therapeutic agents or graft materials are delivered, a dry and isolated site maximizes the delivery of a therapeutic agent or graft material to the appropriate location and prevents blood or other ambient fluids from diluting or dislodging the graft material or the therapeutic agent. The isolated implant site also facilitates targeted therapy to the defect.

Accordingly, there is a need for devices and methods of isolating defects to provide a dry and separated area at which a localized therapy can be delivered.

SUMMARY

This section provides a general summary of the disclosure, and is not a comprehensive disclosure of its full scope or all of its features.

The present teachings provide for an isolation device for repairing a cartilage defect including a syringe and a barrier device. The barrier device is connected to the syringe. The barrier device is sized to surround and contain the cartilage defect, and is configured to provide a seal around the cartilage defect for application of a positive pressure and a negative pressure from the device. The device is configured to provide a localized therapy to the cartilage defect.

The present teachings also provide for an isolation device for repairing a cartilage defect including a syringe, a cannula, and a barrier device. The cannula houses the syringe. The barrier device is sized to surround and contain the cartilage defect. The barrier device is configured to provide a seal around the cartilage defect for application of a positive pressure and a negative pressure from the device, and is movable between a collapsed position within the cannula to an expanded position outside of the cannula. The device is configured to provide a localized therapy to the cartilage defect.

The present teachings further provide for an isolation device for repairing a cartilage defect including a syringe, a cannula housing the syringe, and a barrier device. The barrier device is sized to surround and contain the cartilage defect, and is configured to provide a seal around the cartilage defect for application of a positive pressure and a negative pressure from the device. The barrier device is movable between a collapsed position within the cannula and an expanded position outside of the cannula. The device is configured to provide a localized therapy to the cartilage defect.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Referring to FIGS. 1-5E, the present teachings provide various methods of repairing a cartilage defect 10. Exemplary cartilage defects include those caused by trauma, excessive use (such as sports injuries, for example) or diseases, including, but not limited to, osteoarthritis and osteochondrosis dissecans. The defect can be in the form of a focal cartilage defect or a cartilage abrasion, as non-limiting examples. Exemplary implant sites 12 include, but are not limited to, a patella, a femoral condyle, a femoral head, an acetabulum, or any other articulating joint surfaces.

Referring to FIGS. 1-3D, the isolation device 14 comprises a syringe 16 having a barrier device 18 attached thereto. The syringe 16 comprises a barrel 20 having a proximal end 22, an outlet end 24, a plunger 26, and a plunger seal 28. Collectively, the barrel 20 and the plunger seal 28 define an adjustable chamber 30. The chamber 30 can accommodate vacuum pressure and positive pressure. Actuation of the plunger 26 on the syringe 16 can produce a positive pressure or aspiration or a negative pressure or suction. It is understood that a plurality of chambers 30 or compartmentalized chambers can be used in conjunction with the isolation device 14.

The syringe 16 can be of any suitable size and in various embodiments has a barrel size or volume of less than about 5 cc. As shown in FIGS. 3C and 3D, the syringe 16 can be made of rigid materials adapted to fit within the cannula 32 for arthroscopic procedures or can be made of non-rigid or semi-rigid materials which flex within the cannula 32. A flexible syringe 16 is useful to reach a cartilage defect 10 or regions of the defect where the straight path provided by the cannula 32 is insufficient. The syringe 16 includes a fitting 34 at the outlet end 24 for attachment of a barrier device 18. The barrier device 18 can be removably connected to the syringe 16 using any suitable technique, including a leur fitting, screw-on, press fit, or snap-on, as non-limiting examples.

Figures 1, 2:
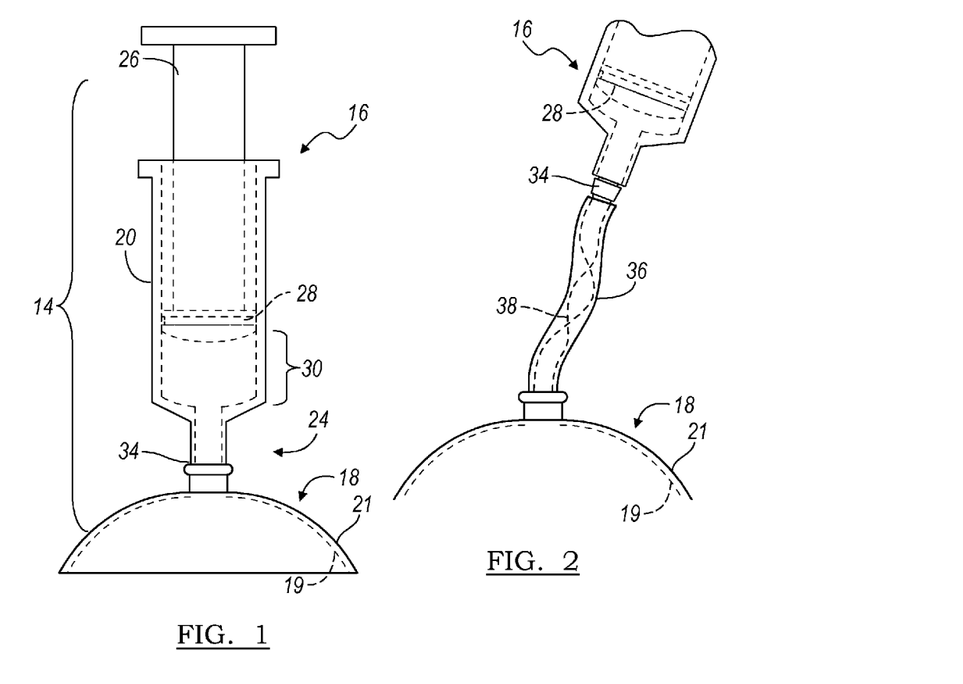
FIG. 1 depicts an isolation device according to the present teachings.
FIG. 2 depicts an isolation device having a mixing chamber according to the present teachings.
Figure 3A:
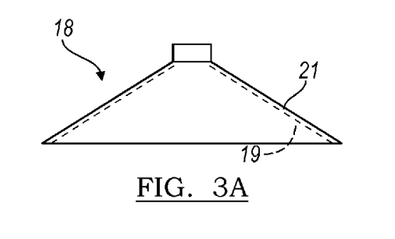
FIGS. 3A, 3B, 3C, and 3D depict various barrier devices according to the present teachings.
Figure 3B:
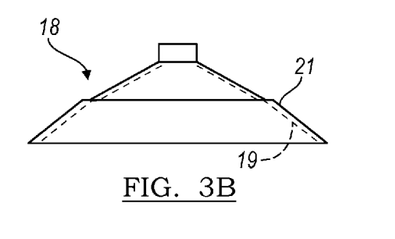
Figure 3C:
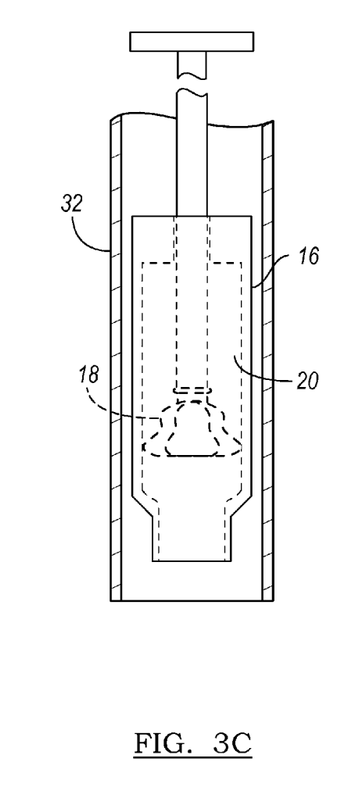
Figure 3D:
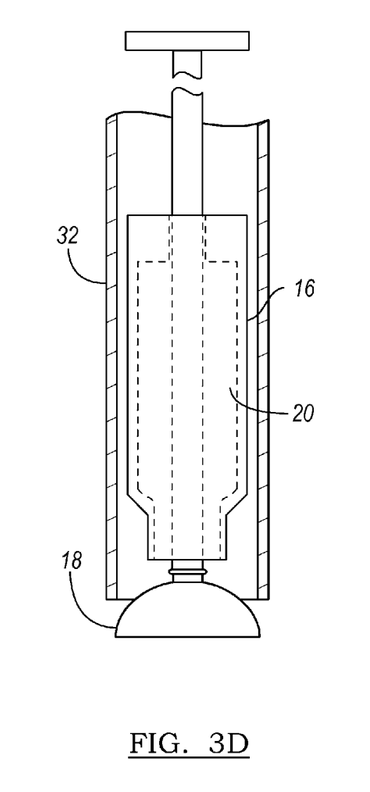

Referring to FIGS. 1 through 3B, the barrier device 18 is shaped for placement about the cartilage defect 10 to separate the cartilage defect 10 from surrounding tissues and/or to bar passage of fluids to the cartilage defect 10. The barrier device 18 comprises an inner surface 19 and an outer surface 21. The inner surface 19 is in contact with the cartilage defect 10 while the outer surface 21 serves as the "barrier" against the ambient environment. As shown in FIGS. 1, 3A, and 3B, the barrier device 18 can be spherical or conical in shape and can optionally be tapered. The barrier device 18 can be rigid, semi-rigid, or flexible. The barrier device 18 can be made of any biocompatible material, including, but not limited to, rubber, plastic, silicone, glass, metal, or combinations thereof. In embodiments where a flexible material is used, the barrier device 18 flexes to provide the removably fixed contact with the cartilage defect 10. Where a rigid material, such as titanium or glass, is used, a gasket can be provided at the base of the inner surface 19 to facilitate suction and/or the removably fixed contact with the cartilage defect 10. The barrier device 18 is designed to accommodate 3-dimensional, planar, arcuate, and jagged surfaces around the cartilage defect 10. In various embodiments, the barrier device 18 is in the form of a suction cup. The inner surface 19 is ideally shaped to match the contour of the surface of the cartilage defect 10.

The size of the barrier device 18 can vary based on the size of the cartilage defect 10. As shown in FIGS. 3C and 3D, the barrier device 18 can be a deployable suction cup, for example, and can be housed within a region of the isolation device 14, for example, the barrel 20 of the syringe 16. As shown in FIG. 3C, the barrier device 18 is compressed in the barrel 20 and expands to full size when deployed out of the barrel 20 as shown in FIG. 3D. The deployable barrier device 18 is attached to the syringe 16 such that, although the barrier device 18 can be deployed from within the syringe 16, the system remains fluid impermeable to maintain the integrity and contents of the syringe 16 until the operator expels the contents of the chamber 30.

As best shown in FIGS. 1 and 2, the barrier device 18 can be directly or indirectly attached to the syringe 16. Where a direct attachment is used, as mentioned above herein, the barrier device 18 is pressed onto, snapped onto, or screwed onto the outlet end 24 of the barrel 30 using an attachment feature or fitting 34. The attachment feature 34 allows for interchangeable barrier devices 18 to be used with the isolation device 14 to accommodate a variety of cartilage defect 10 sizes.

In embodiments where there is an indirect attachment, the barrier device 18 is attached over a tube 36 or hose as shown in FIG. 2. The tube 36 can be used to provide an enhanced flexibility to the isolation device 14. The tube 36 will allow the isolation device 14 to flex and thereby provide surgical freedom, especially in arthroscopic procedures where a series of straight cannulas are used to access the surgical site. The tube 36 can also house a mixing shaft 38. The mixing shaft 38 is useful in embodiments where two separate components are delivered via the isolation device 14 and need to be mixed immediately prior to delivery to the cartilage defect 10. As shown in FIG. 2, the mixing shaft 38 includes an internal helix to facilitate mixing of the components. A diaphragm or other structure can also be used in the mixing shaft 38 to facilitate mixing of the components.

Referring to FIGS. 4A-5E, in various embodiments, the present teachings provide methods of repairing cartilage defects, such as focal cartilage defects, tears, abrasions, and the like. The cartilage defect 10 is identified and shaped to prepare the cartilage defect 10 for a localized therapy. The cartilage defect 10 is then isolated with an isolation device 14 to deliver the localized therapy to the cartilage defect 10. The localized therapy is delivered by use of the isolation device 14.

Figure 4A:
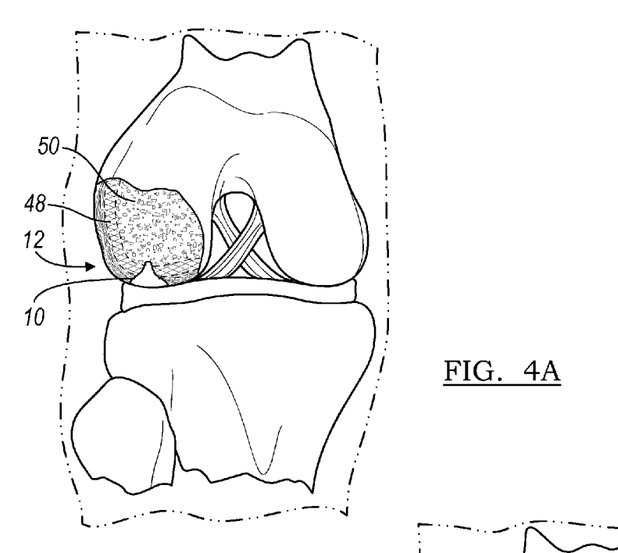
FIGS. 4A and 4B depict surgical methods according to the present teachings.
Figure 4B:
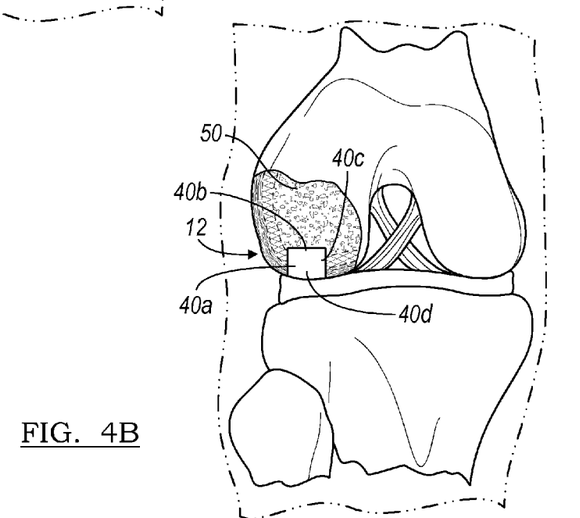

First, a surgical site is prepared either by an open surgical technique or arthroscopic surgical technique. Next, the cartilage defect 10 site is shaped or prepared by removing an area of damaged cartilage to create a defined region such as the plurality of walls 40a, 40b, 40c, 40d about the cartilage defect 10, as shown in FIG. 4B. The removal of the damaged cartilage can include resecting or contouring the cartilage to provide a region of healthy cartilage and/or underlying bone upon which to deliver or perform the localized therapy. The defined walls 40a-40d and the removal of the damaged cartilage provide a placement area 42 for the barrier device 18 on the isolation device 14.

Figure 5A:
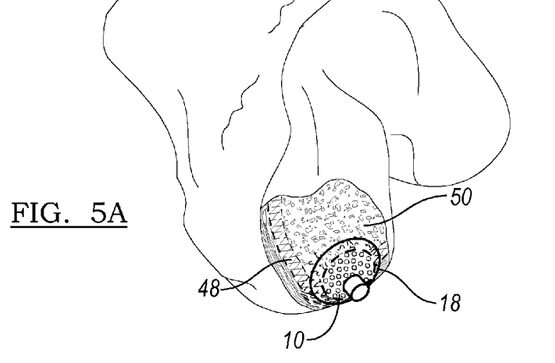
FIGS. 5A through 5E depict surgical methods according to the present teachings.
Figure 5B:
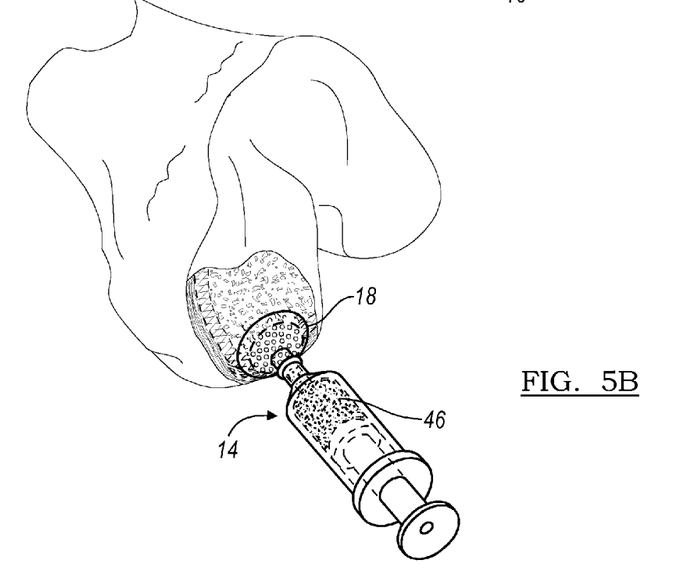
Figure 5C:
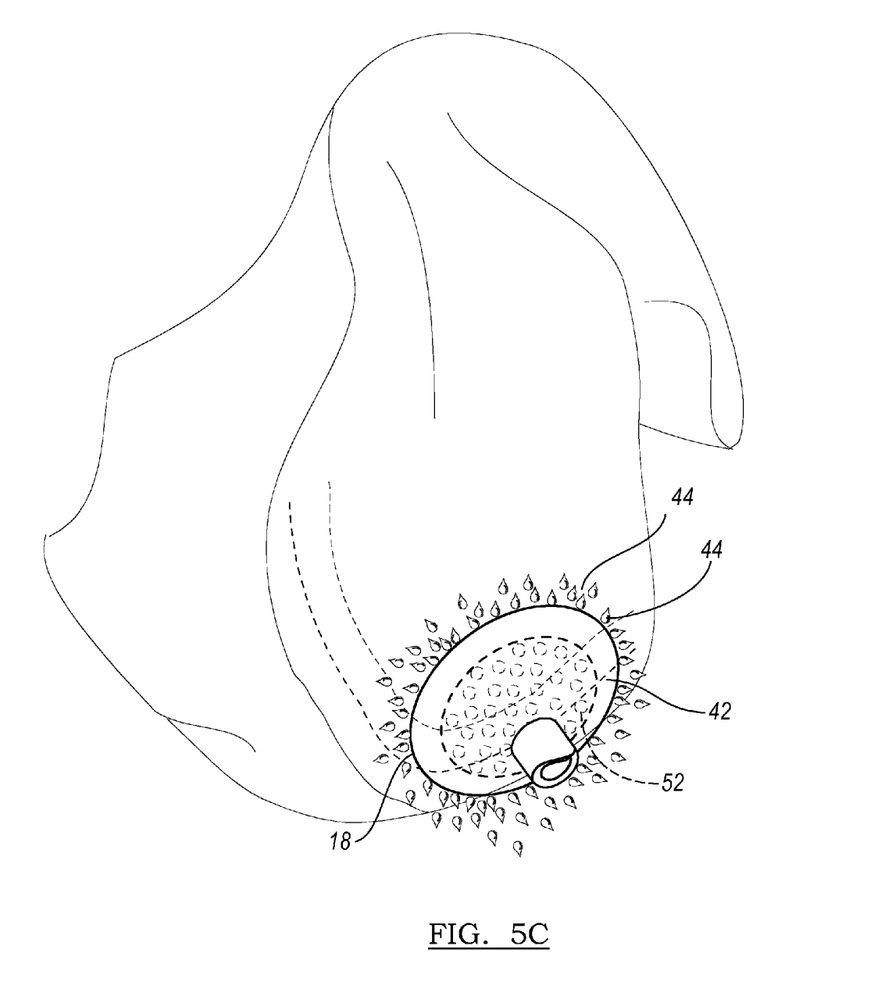
Figure 5D:
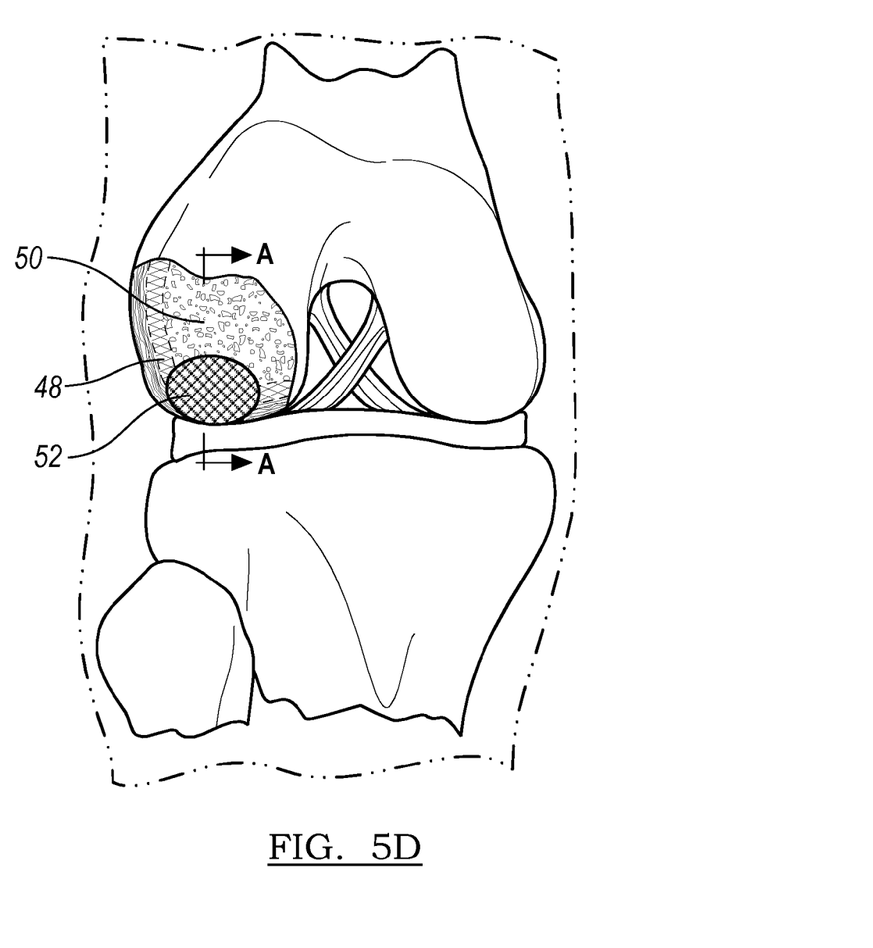
Figure 5E:
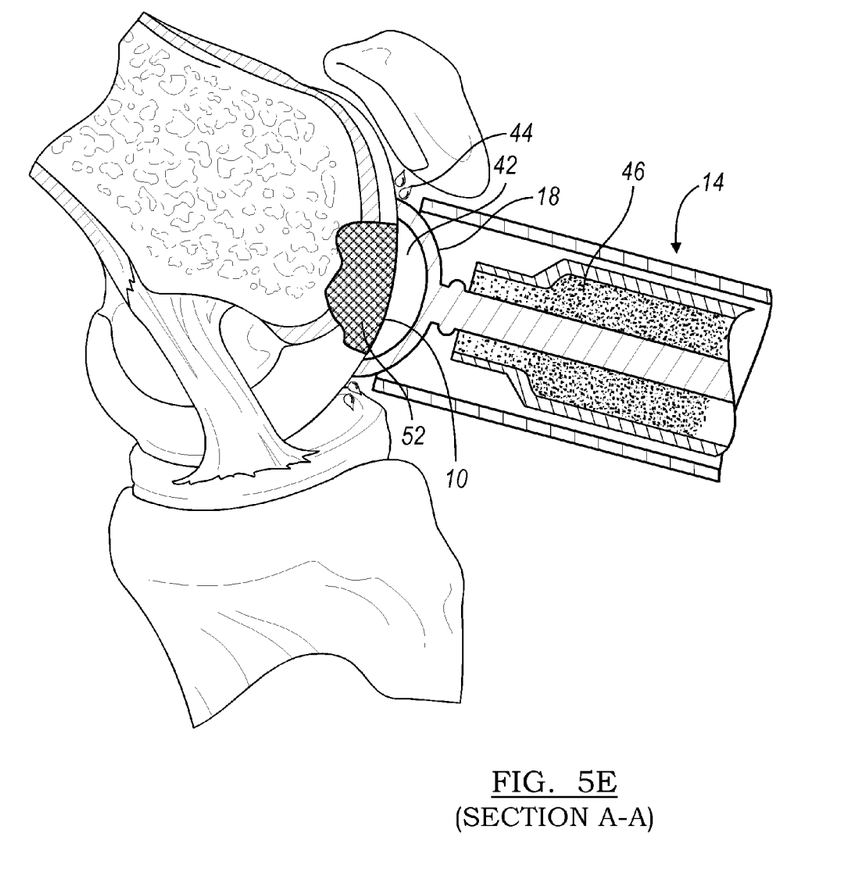

As shown in FIGS. 5A-5E, the defined region can be shaped as a circle, oval, or other rounded shape. This allows a round barrier device 18 to mimic the shape of the defined region, as shown in FIG. 5E. It is understood that the area around the oval defined region and the removal of the damaged cartilage provide the placement area 42 for the barrier device or the isolation device 14.

Providing the healthy surrounding cartilage by shaping or contouring the defect site, maximizes the effectiveness of the localized therapy and facilitates integration of new healthy cartilage into the cartilage defect 10. The damaged cartilage can be trimmed and sized such that the barrier device 18 fits about and contains the entire cartilage defect 10. In various embodiments, the damaged cartilage can be trimmed and sized such that only a region of the cartilage defect 10 is contained by the barrier device 18.

In addition to providing the placement area, microfracture can be performed on the cartilage defect 10 to further prepare the cartilage defect. In microfracture, a small incision is made on the effected cartilage and a portion of the calcified cartilage 48 is removed from the defect site. An awl is then used to create small holes or "microfractures" 52 in the bone under the cartilage defect, as shown in FIGS. 5A-5C, to induce bleeding from the underlying bone into the cartilage defect 10. The blood from the underlying bone 50 contains whole blood and various blood components, including bone marrow and the accompanying stem cells. The induced bleeding forms a blood clot that releases cartilage building cells. It is beneficial to sufficiently shape the surrounding cartilage such that the microfracture blood containing the chondrocytes can integrate into healthy tissue. Microfracture is particularly useful for cartilage injuries, arthritis, lesions, chondral lesions, and traumatic injuries.

After the cartilage defect site 10 is shaped, the barrier device 18 is placed over the cartilage defect 10 to isolate the cartilage defect 10 from an ambient fluid or from a surrounding tissue (both generically depicted as element 44). Ambient fluids include blood, for example, or extracorporeal fluids used to wash the defect site. The surrounding tissue can include various soft tissues, such as muscle, connective tissues, fat, and the surrounding tissue can also include boney tissue. By isolating the cartilage defect 10, the surrounding tissue is pushed away from and contained outside of the cartilage defect 10. This is particularly useful for focal cartilage defects or with microfractures as the isolation prevents ambient tissue from lying over or in the cartilage defect, thereby blocking the delivery of the localized therapy.

The barrier device 18 can be positioned to encase or completely cover the cartilage defect 10. In various embodiments, the barrier device 18 rests on the placement area 42 of surrounding healthy cartilage. Upon pressing the barrier device 18 to the base, the air pressure inside of the barrier device 18 is drastically reduced. The relatively higher atmospheric pressure forces the barrier device 18 to stick, suction onto, or otherwise become removably fixed onto the surface of the healthy surrounding cartilage.

When the barrier device 18 is in place, the localized therapy is then administered. The localized therapy can include delivery of a therapeutic agent 46 or graft material, withdrawing blood from the underlying bone, or aspirating the cartilage defect 10. It is understood that any combination of localized therapies can be used to repair the cartilage defect 10.

In embodiments where the localized therapy includes delivery of a therapeutic agent or graft material, the materials are included at a safe and effective amount that is sufficient to have the desired effect in the human or lower animal subject, without undue adverse side effects (such as toxicity, irritation, or allergic response), commensurate with a reasonable benefit/risk ratio when used in the manner of these teachings. The specific safe and effective amount of the therapeutic agent 46 will vary with such factors as the particular condition being treated, the physical condition of the patient, the nature of concurrent therapy (if any), the specific therapeutic agent 46 used, the specific route of administration and dosage form, the carrier employed, and the desired dosage regimen.

Therapeutic agents 46 useful in the practice of the present teachings include organic molecules, proteins, peptides, antibiotics, analgesics, polysaccharides, glycoproteins, lipoproteins, carbohydrates and polysaccharides, and synthetic and biologically engineered analogs thereof, growth factors, vitamins, minerals, living cells such as chondrocytes, bone marrow cells, undifferentiated and differentiated stem cells, cartilage cells, natural extracts, and combinations thereof. The graft materials can include resorbable polymers such as lactocarbonate; polyurethane urea; polymers and copolymers of trimethylene carbonate, lactic acid, and/or glycolic acid; and combinations thereof, or natural cartilage. Other suitable therapeutic agents 46 include blood products such as platelet rich plasma, concentrated plasma, fibrin, thrombin, fibrinogen, whole blood, etc. The therapeutic agent 46 or graft materials can be in the form of a liquid, a paste, or a gel material.

In various embodiments, the therapeutic agent 46 comprises separated components which are combined in the mixing shaft 38 of the isolation device 14 immediately prior to delivery to the cartilage defect 10. An example is a mixture of thrombin and plasma. In such embodiments, the separated thrombin and plasma combine in the mixing shaft 38 and the appropriate mixing is achieved through the length of mixing shaft 38 as shown in FIG. 2. The mixing can also be facilitated with the diaphragms or helices as mentioned above herein.

The therapeutic agent 46 can be delivered from within the isolation device 14 with sufficient pressure to cause the therapeutic agent to transcend a calcified cartilage layer 48 at the cartilage defect 10 and infiltrate the underlying bone 50. Infiltrating the underlying bone 50 and tissue with the therapeutic agent 46, such as a growth factor, is advantageous as compared to placement of the therapeutic agent 46 only on the surface of the defect because infiltrating the underlying bone 50 and tissue expedites healing at the focal cartilage defect 10 and reduces the chances of unintentional dislodging of the therapeutic agent or the graft material from the defect. The therapeutic agent 46 can also be delivered to rest within the cartilage defect and not transcend the calcified cartilage layer 48 and the underlying bone 50. The therapeutic agent 46 fills the shaped cartilage defect 10 as shown in FIG. 5D.

In other various embodiments, the localized therapy includes drawing blood material from the underlying bone 50 into the cartilage defect 10 using suction. The cartilage defect 10 is shaped to expose the underlying bone 50 and isolated from ambient fluids and materials as described above herein. A negative pressure is applied from the isolation device 14 to draw a blood material (including bone marrow and stem cells) from the underlying bone 50 into the cartilage defect 10. The pressure applied is an amount sufficient to draw blood material from deep within the cancellous bone. Those skilled in the art appreciate that the combination of syringe size, cartilage defect size, and the desired amount of material removed by the negative pressure are considered in selecting the amount of negative pressure to apply.

The isolation device 14 can also be used to apply a positive pressure to aspirate and dry the region. Aspirating the region can be used to prepare the cartilage defect 10 for drawing blood from the underlying bone 50. Aspirating the region can also be used to prepare a dry cartilage defect or to remove debris from the cartilage defect 10 prior to application of a therapeutic agent or a graft material.

In still other embodiments, the localized therapy can include a UV curable localized therapy. The cartilage defect 10 is shaped to expose the underlying bone 50 and the region is isolated from ambient fluids and materials as detailed above herein. A UV curable composition is then delivered to the isolated region with the isolation device 14. The UV curable composition 46 is cured by exposing the therapeutic agent 46 to the UV light while the barrier device 18 is isolating the region.

After the isolation device 14 is placed over the cartilage defect 10 to isolate the defect from the ambient fluids and tissue, a UV light source is placed at the cartilage defect 10 site through the isolation device 14, a nearby cannula, or through a side port or second arthroscopic opening. For example, the UV light can be delivered to the surface of a barrier device 18 that is sufficiently transparent or contains regions of the transparency to facilitate passage of the UV light therethrough. Where the UV light is administered through the syringe 16 of the isolation device 14, a fiber optic cable can be employed to fit in the syringe 16. The duration and intensity of the UV light application is selected based on the size of the cartilage defect and the UV curable monomers employed.

The isolation device 14 is advantageously used with UV curable localized therapy because the UV curable components can be sensitive to aqueous environments such as in vivo conditions and/or the curing time may be increased in aqueous environments. The UV curable components useful in the present teachings include those curable monomers which are biocompatible and which form biocompatible polymers upon curing. It is also advantageous to minimize the heat generation from the polymerization reactions and application of the UV light during curing.

It is understood that the therapies and surgical techniques detailed above herein can be applied to an implant at the cartilage defect 10. For example, the isolation device 14 can be used to apply therapies to an osteochondral plug, over a bone screw, over a staple, or other implant. Example materials to which the isolation device 14 can deliver a therapy include, but are not limited to, calcium phosphates, polymers and co-polymers of lactic acid and glycolic acid, calcium sulfate, collagen, or an allograft material.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. An isolation device for repairing a cartilage defect comprising:
   a syringe;
   a barrier device connected to the syringe, the barrier device is sized to surround and contain the cartilage defect, and the barrier device is configured to provide a seal around the cartilage defect for application of a positive pressure and a negative pressure from the device; and
   a cannula, the syringe and the barrier device being housed within the cannula, the barrier device being configured to be moved between a first position within the cannula and a second position outside of the cannula;
   wherein the device is configured to provide a localized therapy to the cartilage defect.

2. The isolation device of claim 1, wherein the syringe includes a plunger.

3. The isolation device of claim 1, wherein the barrier device is collapsible.

4. The isolation device of claim 1, wherein the barrier device is a dome-shaped suction cup.

5. The isolation device of claim 1, further comprising a flexible tube between the syringe and the barrier device.

6. The isolation device of claim 5, wherein the flexible tube includes a mixer.

7. The isolation device of claim 1, wherein the localized therapy includes at least one of the following: delivering a therapeutic agent; withdrawing blood from an underlying bone; applying a negative pressure to the cartilage defect; applying a positive pressure; aspirating the cartilage defect; or delivering a UV curable composition.

8. The isolation device of claim 1, wherein the barrier device is collapsed in the first position and expanded in the second position.

9. An isolation device for repairing a cartilage defect comprising:
   a chamber configured to house a therapeutic agent;
   a suction cup in fluid communication with the chamber; and
   a cannula housing the chamber;
   wherein the suction cup is movable between a collapsed position within the cannula and an expanded position outside of the cannula to provide a localized therapy to the cartilage defect.

10. The isolation device of claim 9, wherein the chamber is included with a syringe; and
    wherein the suction cup is movable between the collapsed position within the syringe and the expanded position outside the syringe.

11. The isolation device of claim 9, wherein the suction cup is sized and shaped to surround and contain the cartilage defect, and provide a seal around the cartilage defect for application of a positive pressure and a negative pressure from the device.

12. The isolation device of claim 9, further comprising a flexible tube between the suction cup and the chamber, the flexible tube housing a mixer.

13. The isolation device of claim 12, wherein the localized therapy comprises delivery of a therapeutic agent including a first component and a second component that are combined in the flexible tube by the mixer.

14. The isolation device of claim 9, wherein the localized therapy includes at least one of the following: delivering a therapeutic agent; withdrawing blood from an underlying bone; applying a negative pressure to the cartilage defect; applying a positive pressure; aspirating the cartilage defect; or delivering a UV curable composition.

15. An isolation device for repairing a cartilage defect comprising:
    a syringe;
    a cannula housing the syringe; and
    a barrier device sized to surround and contain the cartilage defect, the barrier device is configured to provide a seal around the cartilage defect for application of a positive pressure and a negative pressure from the device, the barrier device is movable between a collapsed position within the cannula and an expanded position outside of the cannula;
    wherein the device is configured to provide a localized therapy to the cartilage defect.

16. The isolation device of claim 15, wherein the barrier device is a dome-shaped suction cup movable between the collapsed position within the syringe and the expanded position outside the syringe.

17. The isolation device of claim 15, further comprising a flexible tube between the syringe and the barrier device, the flexible tube including a mixer.

18. The isolation device of claim 15, wherein the localized therapy includes at least one of the following: delivering a therapeutic agent; withdrawing blood from an underlying bone; applying a negative pressure to the cartilage defect; applying a positive pressure; aspirating the cartilage defect; or delivering a UV curable composition.

19. The isolation device of claim 15, wherein the localized therapy comprises delivery of a therapeutic agent including a first component and a second component that are combined in a shaft including a mixer between the syringe and the barrier device.

* * * * *